US011517880B2

(12) United States Patent
Yook et al.

(10) Patent No.: US 11,517,880 B2
(45) Date of Patent: Dec. 6, 2022

(54) CARBON-BASED NOBLE METAL-TRANSITION METAL CATALYST ENABLING HIGH SELECTIVE CONVERSION AND PRODUCTION METHOD THEREFOR

(71) Applicant: HANWHA SOLUTIONS CORPORATION, Seoul (KR)

(72) Inventors: Sun Woo Yook, Seongnam-si (KR); Jeong Kwon Kim, Seoul (KR); Wan Jae Myeong, Daejeon (KR); Bong Sik Jeon, Daejeon (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 83 days.

(21) Appl. No.: 16/958,493

(22) PCT Filed: Dec. 27, 2018

(86) PCT No.: PCT/KR2018/016746
§ 371 (c)(1),
(2) Date: Jun. 26, 2020

(87) PCT Pub. No.: WO2019/132537
PCT Pub. Date: Jul. 4, 2019

(65) Prior Publication Data
US 2021/0060534 A1    Mar. 4, 2021

(30) Foreign Application Priority Data
Dec. 29, 2017  (KR) .................. 10-2017-0183451

(51) Int. Cl.
*B01J 21/18*  (2006.01)
*B01J 23/62*  (2006.01)
(Continued)

(52) U.S. Cl.
CPC .......... *B01J 21/185* (2013.01); *B01J 23/626* (2013.01); *B01J 35/1019* (2013.01);
(Continued)

(58) Field of Classification Search
CPC .... B01J 21/185; B01J 23/626; B01J 35/1019; B01J 35/1023; B01J 35/1042; B01J 37/0207; B01J 37/0213; C07C 29/149
(Continued)

(56) References Cited

U.S. PATENT DOCUMENTS 6,294,703 B1   9/2001  Hara et al.
6,495,730 B1   12/2002 Konishi et al.
(Continued)

FOREIGN PATENT DOCUMENTS

CN    1911504 A    2/2007
CN    101982236 A   3/2011
(Continued)

OTHER PUBLICATIONS

Rylander, P.N. (1967) Catalytic Hydrogenation Over Platinum Metals, Academic Press, 550 pp [Office action cites p. 229].*

*Primary Examiner* — Brian A McCaig
(74) *Attorney, Agent, or Firm* — Sughrue Mion, PLLC

(57) ABSTRACT

Provided are a carbon-based noble metal-transition metal composite catalyst enabling high selective conversion of a carboxylic acid functional group into an alcohol functional group by pre-treating a carbon carrier including a predetermined ratio or more of mesopores, and a production method therefor.

16 Claims, 2 Drawing Sheets

(51) Int. Cl.
    *B01J 35/10*     (2006.01)
    *B01J 37/02*     (2006.01)
    *C07C 29/149*     (2006.01)

(52) U.S. Cl.
    CPC ....... *B01J 35/1023* (2013.01); *B01J 35/1042* (2013.01); *B01J 37/0207* (2013.01); *B01J 37/0213* (2013.01); *C07C 29/149* (2013.01)

(58) Field of Classification Search
    USPC ........................................................ 502/185
    See application file for complete search history.

(56) References Cited

U.S. PATENT DOCUMENTS

| | | | |
|---|---|---|---|
| 9,108,895 | B2 | 8/2015 | Liu et al. |
| 2006/0183936 | A1 | 8/2006 | Grass et al. |
| 2014/0121400 | A1 | 5/2014 | Liu et al. |
| 2016/0296911 | A1* | 10/2016 | Bohringer ................ B01J 20/20 |

FOREIGN PATENT DOCUMENTS

| | | |
|---|---|---|
| CN | 104549251 A | 4/2015 |
| CN | 106311201 A | 1/2017 |
| CN | 107469813 A | 12/2017 |
| JP | 10-71332 A | 3/1998 |
| JP | 2001-46874 A | 2/2001 |
| JP | 2014-177422 A | 9/2014 |
| JP | 2015-54828 A | 3/2015 |
| KR | 10-2013-0001876 A | 1/2013 |
| KR | 10-2014-0064352 A | 5/2014 |
| KR | 10-2015-0079750 A | 7/2015 |
| KR | 10-2015-0109607 A | 10/2015 |
| WO | 2015/156582 A1 | 10/2015 |
| WO | 2017/059192 A1 | 4/2017 |

\* cited by examiner

CARBON-BASED NOBLE METAL-TRANSITION METAL CATALYST ENABLING HIGH SELECTIVE CONVERSION AND PRODUCTION METHOD THEREFOR

CROSS REFERENCE TO RELATED APPLICATIONS

This application is a National Stage of International Application No. PCT/KR2018/016746 filed Dec. 27, 2018, claiming priority based on Korean Patent Application No. 10-2017-0183451 filed Dec. 29, 2017.

TECHNICAL FIELD

The present invention relates to a carbon-based noble metal-transition metal catalyst enabling high selective conversion and a production method therefor, and more particularly, to a carbon-based noble metal-transition metal composite catalyst enabling high selective conversion of a carboxylic acid functional group into an alcohol functional group by pre-treating a carbon carrier including a predetermined ratio or more of mesopores, and a production method therefor.

BACKGROUND ART

Diol is widely used as a base industrial material such as polyesters, polyurethanes, vanishes, and adhesives pharmaceuticals. In addition, the demand for eco-friendly and biodegradable diols has increased significantly in recent years. These diol compounds can be converted from dicarboxylic acid or its derivatives through a hydroprocessing catalyst. Most existing catalyst processes that enable this conversion are catalyst processes based on a Cu—Cr or Zr—Cr based catalyst, ruthenium oxide, ruthenium-carbon composites, and the like. However, such catalyst processes require operating conditions of high pressure (200 bar to 300 bar). Therefore, it is essential to develop catalysts that can be operated under relatively low pressure conditions.

Among a plurality of diol compounds, when cyclohexanedimethanol (CHDM) is used to replace ethylene glycol and other polyols in producing polyester resins, the CHDM has attracted great attention because of its high thermal stability, insulation, transparency, and chemical resistance. Dimethylterephthalate (DMT) is produced by esterification of terephthalic acid (TPA) with methanol and then CHDM is industrially produced through two additional hydrogenation processes. However, in recent years, efforts have been made to produce CHDM through a single-step hydrogenation reaction in cyclohexanedicarboxylic acid (CHDA) so as to reduce production costs and simplify processes.

Therefore, in the present invention, a method for synthesizing a catalyst that efficiently produces cyclohexanedimethanol (CHDM), which is a target diol, by using cyclohexanedicarboxylic acid (CHDA) as a representative material of dicarboxylic acid will be described.

Mitsubishi Chemical (MCC) has patented a RuPtSn/C catalyst as a CHDA-to-CHDM catalyst (U.S. Pat. No. 6,294,703), but this patent has a disadvantage that the catalyst is expensive due to Pt. Asahi Kasei suggested a Ru—Sn—Re/C catalyst as a CHDA-to-CHDM catalyst (U.S. Pat. No. 6,495,730). However, despite the use of expensive Re, the yield of CHDM was only 75%. Lotte Chemical suggested Y-zeolite as a carrier for RuPtSn (WO 2015-156582), but this also incurs a high catalyst cost. In order to improve a RuSn/$Al_2O_3$ catalyst that is an existing prior patent (CN 1911504), Sinopec applied for a patent that used a carrier of a catalyst by coating a carbon layer over $Al_2O_3$(CN 104549251). However, a multi-step synthesis process is required so as to synthesize an $Al_2O_3$ carrier coated with a carbon layer suggested in the above patent. In addition, due to characteristics of a CHDA reaction, a reaction solution is in a high temperature acidic condition. Thus, there is a high possibility that an Al leaching problem of $Al_2O_3$ in which hydrothermal stability is lower than carbon will occur. Zhang Xiaoou applied for a patent that the performance and lifespan of catalyst could be secured when ordered mesoporous carbon (OMC) having a pore volume of 1.5 ml/g to 2.5 ml/g, a specific surface area of 1,000 $m^2$/g to 2,000 $m^2$/g, and a pore size of 3 nm to 10 nm was used as a RuSn catalyst carrier (CN 101982236A). However, in the case of the OMC that satisfies the physicochemical properties suggested above, a synthesis method includes a multi-step process. This increases production costs and is unfavorable for use in actual commercial facilities. In addition, in the case of the OMC, pores are formed in a reverse phase of a material used as a template. Thus, when pore connectivity of the template used is low, the mechanical strength of a carbon framework forming an OMC structure is likely to be lower than that of a conventional carbon material. In the prior patent (CN 101982236A), an aqueous hydrogen peroxide solution or an aqueous hydrochloric acid solution was used at room temperature as a pre-treatment of a carbon carrier. In this case, the amount of oxygen functional groups introduced on the surface of the carbon carrier is small. Thus, it is disadvantageous in effectively immobilizing a Ru—Sn active metal.

DESCRIPTION OF EMBODIMENTS

Technical Problem

The present invention aims to solve the above-described problems of the related art and the technical problems requested from the past.

An object of the present invention is to provide a carbon-based noble metal-transition metal composite catalyst enabling high selective conversion of a carboxylic acid functional group into an alcohol functional group by pre-treating a carbon carrier including a predetermined volume ratio or more of mesopores relative to the total pores, so that a conventional catalyst synthesis process is reduced or improved to exhibit high activity at a low cost, and a production method therefor

Solution to Problem

In order to achieve the objects, a carbon-based noble metal-transition metal catalyst enabling selective conversion according to the present invention is a hydrogenation catalyst using porous carbon as a carrier.

The carbon may be 50% or more in a volume ratio of mesopores having a pore size of 2 nm to 50 nm among the total pores, and an amount of an active metal may be in a range of 1 part by weight to 20 parts by weight based on 100 parts by weight of the carrier.

In one preferred embodiment of the present invention, the carbon may include at least one selected from the group consisting of activated carbon, carbon black, graphite, graphene, ordered mesoporous carbon (OMC), and carbon nanotubes.

In one preferred embodiment of the present invention, the active metal may include: one or more noble metals selected from the group consisting of palladium (Pd), rhodium (Rh), ruthenium (Ru), and platinum (Pt); and one or more transition metals selected from the group consisting of tin (Sn), iron (Fe), rhenium (Re), and gallium (Ga).

In one preferred embodiment of the present invention, the noble metal may be ruthenium, and the transition metal may be tin.

In one preferred embodiment of the present invention, the carbon carrier may be pre-treated with an aqueous nitric acid ($HNO_3$) solution.

In one preferred embodiment of the present invention, the aqueous nitric acid ($HNO_3$) solution may include 1 part by weight to 50 parts by weight of nitric acid based on 100 parts by weight of the solution.

In one preferred embodiment of the present invention, the carbon may have a specific surface area of 100 $m^2$/g to 1,500 $m^2$/g and a pore volume of 0.1 ml/g to 1.5 ml/g.

In one preferred embodiment of the present invention, the carbon may be ordered mesoporous carbon (OMC) having ordered mesopores of 2 nm to 25 nm and having a three-dimensional rod-shaped or three-dimensional tubular pore structure. That is, since the active metal is supported in the carbon carrier arranged in the three-dimensional ordered mesopore structure, the catalyst activity is high as compared to the existing catalyst, thereby improving selectivity and generation rate.

The present invention provides a use of a hydrogenation catalyst for hydrogenating a carboxylic acid group to an alcohol group by using the catalyst and a method for producing the catalyst, wherein the carbon carrier is pre-treated with an aqueous nitric acid ($HNO_3$) solution including 1 part by weight to 50 parts by weight of nitric acid once or more times.

In one preferred embodiment of the present invention, the pre-treatment process may be performed in a temperature range of 50° C. to 150° C.

In one preferred embodiment of the present invention, the pre-treatment process may be performed for 1 hour to 10 hours.

In one preferred embodiment of the present invention, the pre-treatment process may be performed before the active metal is supported.

The present invention provides a hydrogenation method for hydrogenating a carboxylic acid functional group, an aldehyde functional group, or a ketone functional group to an alcohol functional group by using the catalyst.

In one preferred embodiment of the present invention, a hydrogenation reaction pressure may be 2 MPa to 15 MPa, a reaction temperature may be 140° C. to 280° C., and a reaction time may be 0.5 hours to 10 hours.

In one preferred embodiment of the present invention, the carboxylic acid may include oxalic acid, malonic acid, succinic acid, glutaric acid, adipic acid, pimelic acid, suberic acid, azelaic acid, sebacic acid, phthalic acid, isopthalic acid, terephthalic acid, formic acid, acetic acid, caproic acid, caprylic acid, lauric acid, myristic acid, palmitic acid, stearic acid, isostearylic acid, oleic acid, maleic acid, adipic acid, sebacic acid, cyclohexane carboxylic acid, and benzoic acid.

In one preferred embodiment of the present invention, the aldehyde functional group may include formaldehyde, propionaldehyde, n-butylaldehyde, isobutylaldehyde, valeraldehyde, 2-methylbutylaldehyde, 3-methylbutylaldehyde, 2,2-dimethylpropionaldehyde, capronaldehyde, 2-methylvaleraldehyde, 3-methylvaleraldehyde, 4-methylvaleraldehyde, 2-ethylbutyl aldehyde, 2,2-dimethylbutylaldehyde, 3,3-dimethylbutylaldehyde, caprylaldehyde, caprinealdehyde, and glutalaldehyde.

In one preferred embodiment of the present invention, the ketone functional group may include acetone, butanone, pentanone, hexanone, cyclohexanone, and acetophenone.

Advantageous Effects of Disclosure

As described above, in the carbon-based noble metal-transition metal catalyst enabling high selective conversion according to the present invention, since the carbon carrier including a predetermined ratio of mesopores is pre-treated and used, the conversion reaction rate of cyclohexane dicarboxylic acid (CHDA) is improved to exhibit high activity at a low cost.

BEST MODE

Figure 1:
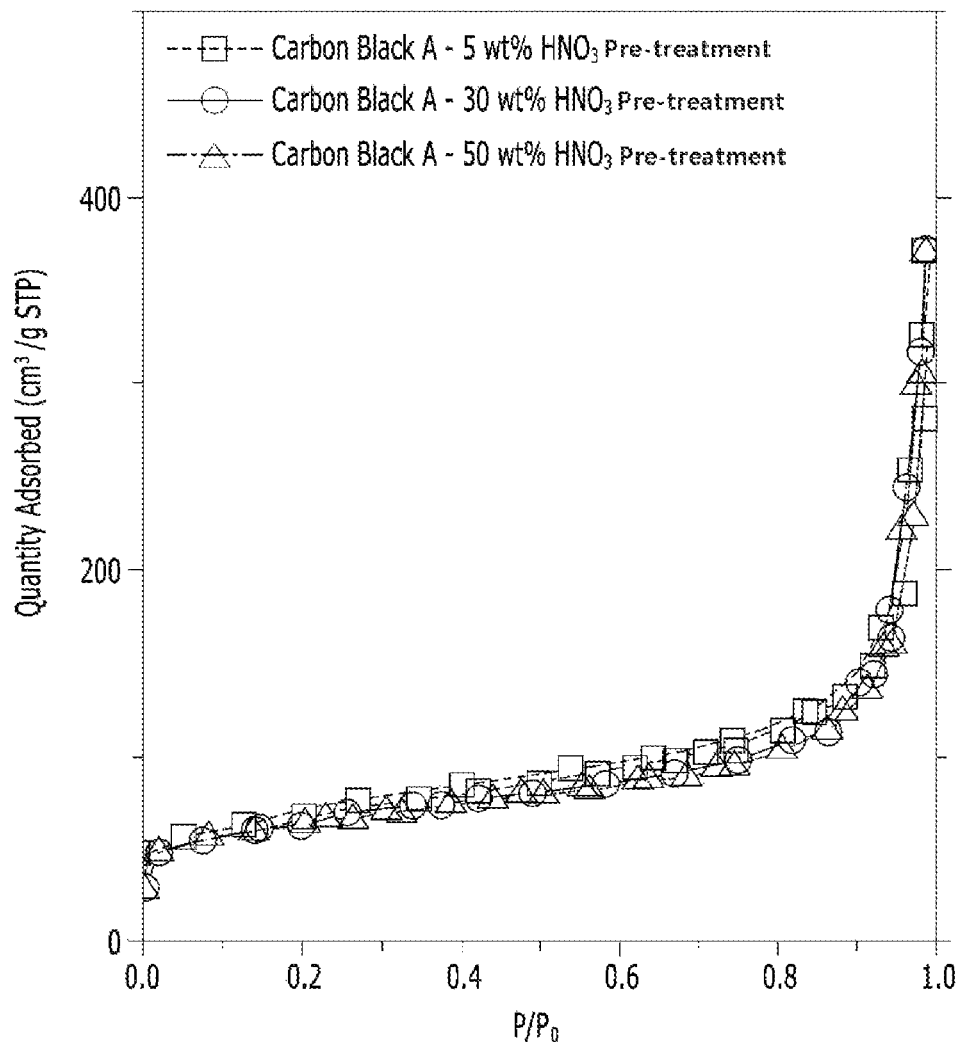
FIG. 1 is a graph showing the results of nitrogen physical adsorption analysis of nitric acid-treated carbon black A carriers according to an embodiment of the present invention.

The present invention will be described with reference to specific embodiments and the accompanying drawings. The embodiments will be described in detail in such a manner that the present invention may be carried out by those of ordinary skill in the art. It should be understood that various embodiments of the present invention are different, but need not be mutually exclusive. For example, certain shapes, structures, and features described herein may be implemented in other embodiments without departing from the spirit and scope of the present invention in connection with one embodiment.

Therefore, the following detailed description is not to be taken in a limiting sense, and the scope of the present invention is to be limited only by the appended claims and the entire scope of equivalents thereof, if properly explained.

In addition, unless otherwise specified in the present specification, the term "substitution" or "substituted" means that one or more hydrogen atoms in the functional groups of the present invention are substituted with one or more substituents selected from the group consisting of a halogen atom (—F, —Cl, —Br, or —I), a hydroxy group, a nitro group, a cyano group, an amino group, an amidino group, a hydrazine group, a hydrazone group, a carboxyl group, an ester group, a ketone group, a substituted or unsubstituted alkyl group, a substituted or unsubstituted alicyclic organic group, a substituted or unsubstituted aryl group, a substituted or unsubstituted alkenyl group, a substituted or unsubstituted alkynyl group, a substituted or unsubstituted heteroaryl group, and a substituted or unsubstituted heterocyclic group. These substituents may be linked to each other to form a ring.

In the present invention, unless otherwise specified, the term "substituted" means that a hydrogen atom is substituted with a substituent such as a halogen atom, a $C_1$-$C_{20}$ hydrocarbon group, a $C_1$-$C_{20}$ alkoxy group, and a $C_6$-$C_{20}$ aryloxy group.

In addition, unless otherwise specified, the term "hydrocarbon group" refers to a linear, branched, or cyclic saturated or unsaturated hydrocarbon group. The alkyl group, the alkenyl group, the alkynyl group, and the like may be linear, branched, or cyclic.

In addition, unless otherwise specified in the present specification, the term "alkyl group" refers to a $C_1$-$C_{30}$ alkyl group and the term "aryl group" refers to a $C_6$-$C_{30}$ aryl group. In the present specification, the term "heterocyclic group" refers to a group in which one to three heteroatoms selected from the group consisting of O, S, N, P, Si, and any combination thereof are contained in one ring. Examples of the heterocyclic group may include pyridine, thiophene, and pyrazine, but the present invention is not limited thereto.

In the detailed description of the present invention, the term "dicarboxylic acid" refers to an organic acid having two carboxylic acid functional groups in one molecule. For example, the molecular formula of the dicarboxylic acid is HOOC—R—COOH. In the present invention, R is preferably an alkyl group or an aryl group.

Hereinafter, embodiments of the present invention will be described with reference to the accompanying drawings, so that those of ordinary skill in the art can easily carry out the present invention.

The present invention solves the above problems by providing a carbon-based noble metal-transition metal catalyst enabling high selective conversion, wherein, as a hydrogenation catalyst using porous carbon as a carrier, a carbon carrier is pre-treated by using an aqueous nitric acid solution, the carbon is 50% or more in a volume ratio of mesopores having a pore size of 2 nm to 50 nm among the total pores, and an amount of an active metal is in a range of 1 part by weight to 20 parts by weight based on 100 parts by weight of the carrier.

Such a catalyst can exhibit high activity at a low cost by improving a conversion reaction rate of cyclohexane dicarboxylic acid (CHDA) described above.

Hereinafter, the composition of the carbon-based noble metal-transition metal catalyst enabling high selective conversion will be described in more detail.

The carbon carrier is not particularly limited. At least one selected from the group consisting of activated carbon, carbon black, graphite, graphene, ordered mesoporous carbon (OMC), and carbon nanotubes may be used as the carbon carrier. Preferably, the carbon carrier may be carbon black having a high ratio of mesopores among the total pores. In a specific example, the activated carbon may be SX ULTRA, CGSP, PK1-3, SX 1G, DRACO S51HF, CA-1, A-51, GAS 1240 PLUS, KBG, CASP, and SX PLUS, and the carbon black may be BLACK PEARLS®, ELFTEX®, VULCAN®, MOGUL®, MONARCH®, EMPEROR, and REGAL®. However, the present invention is not limited thereto.

According to the present invention, the carbon in the carbon carrier may be 50% or more in a volume ratio of mesopores having a pore size of 2 nm to 50 nm in the total pores. Preferably, the carbon in the carbon carrier is 70% or more in a volume ratio of mesopores among the total pores. More preferably, the carbon in the carbon carrier may be 75% or more in a volume ratio of mesopores among the total pores.

In this case, when the volume ratio of the mesopores is less than 50%, there may be micro-transfer rate problems in the carbon carrier of the reactant and the product. When the average size of the pores exceeds 50 nm, the physical strength of the carrier may be weak. Therefore, the above range is preferable.

In addition, according to the present invention, the carbon includes ordered mesoporous carbon (OMC) having a specific surface area (BET) of 100 $m^2$/g to 1,500 $m^2$/g. In addition, according to the present invention, the carbon includes ordered mesoporous carbon (OMC) having a specific surface area (BET) of 200 $m^2$/g to 1,500 $m^2$/g. In this case, when the specific surface area of the carbon is less than 100 $m^2$/g, high dispersion of active metals (Ru, Sn) may be difficult. When the specific surface area of the carbon exceeds 1,500 $m^2$/g, the ratio of the mesopores may decrease. Therefore, the above range is preferable.

The active metal may include: one or more noble metals selected from the group consisting of palladium (Pd), rhodium (Rh), ruthenium (Ru), and platinum (Pt); and one or more transition metals selected from the group consisting of tin (Sn), iron (Fe), rhenium (Re), and gallium (Ga). However, the present invention is not limited thereto.

According to the present invention, an amount of the noble metal may be in a range of 1 part by weight to 20 parts by weight based on 100 parts by weight of the carrier. Preferably, the amount of the noble metal may be in a range of 3 parts by weight to 8 parts by weight. An amount of the transition metal may be in a range of 1 part by weight to 20 parts by weight based on 100 parts by weight of the carrier. Preferably, the amount of the transition metal may be in a range of 3 parts by weight to 8 parts by weight.

In addition, in some cases, the carbon carrier of the catalyst according to the present invention includes micropores at an appropriate ratio in addition to the mesoporosity of a medium size. Preferably, the volume ratio of the micropores in the total pores may be 0% to 25%. In this case, when the volume ratio of the micropores exceeds 25%, there may be micro-transfer rate problems in the carbon carrier of the reactant and the product. Therefore, the above range is preferable.

The present invention provides a method for producing a carbon-based noble metal-transition metal catalyst enabling high selective conversion, wherein a carbon carrier is pre-treated with an aqueous nitric acid ($HNO_3$) solution once or more times.

According to the present invention, a process of pre-treating the carbon carrier with the aqueous nitric acid ($HNO_3$) solution once or more times is performed. The aqueous nitric acid ($HNO_3$) solution may include 1 part by weight to 50 parts by weight of nitric acid based on 100 parts by weight of the solution. Preferably, the aqueous nitric acid ($HNO_3$) solution may be an aqueous solution including 5 parts by weight to 40 parts by weight of nitric acid based on 100 parts by weight of the solution. More preferably, the aqueous nitric acid ($HNO_3$) solution may be an aqueous solution including 5 parts by weight to 35 parts by weight of nitric acid based on 100 parts by weight of the solution.

When the pre-treatment is performed with less than 1 part by weight of nitric acid based on 100 parts by weight of the solution, it may be difficult to expect the desired activity of the catalyst. When the pre-treatment is performed with 50 parts by weight or more of nitric acid based on 100 parts by weight of the solution, the increase in the acidity of the surface of the carbon carrier and the poisoning of the active metal by oxygen functional groups may cause the reduction in the activity of the catalyst and the collapse of the carbon carrier structure. Therefore, the above range is preferable.

According to the present invention, the pre-treatment process may be performed in a temperature range of 70° C. to 150° C., and preferably 80° C. to 110° C. In this case, when the temperature of the pre-treatment process is less than 70° C., the introduction of oxygen functional groups into the surface of the carbon carrier may be lowered. When the temperature of the pre-treatment process exceeds 150° C., the carbon carrier structure may collapse. Therefore, the above range is preferable.

The present invention may provide a hydrogenation method for converting a dicarboxyl group into a dialcohol group. The present invention may be applied to, for example, a hydrogenation method for hydrogenating carboxylic acids, aldehydes and ketones by using the catalyst. In a specific example, according to the present invention, a cyclohexane dimethanol (CHDM) may be prepared through a cyclohexane dicarboxylic acid (CHDA) hydroprocessing reaction on the catalyst.

The carboxylic acid is not particularly limited and may include, for example, oxalic acid, malonic acid, succinic acid, glutaric acid, adipic acid, pimelic acid, suberic acid, azelaic acid, sebacic acid, phthalic acid, isopthalic acid, terephthalic acid, formic acid, acetic acid, caproic acid, caprylic acid, lauric acid, myristic acid, palmitic acid, stearic acid, isostearylic acid, oleic acid, maleic acid, adipic acid, sebacic acid, cyclohexane carboxylic acid, and benzoic acid.

In addition, examples of the aldehydes having the aldehyde functional group may include formaldehyde, propionaldehyde, n-butylaldehyde, isobutylaldehyde, valeraldehyde, 2-methylbutyl aldehyde, 3-methylbutylaldehyde, 2,2-dimethylpropionaldehyde, capronaldehyde, 2-methylvaleraldehyde, 3-methylvaleraldehyde, 4-methylvaleraldehyde, 2-ethylbutylaldehyde, 2,2-dimethylbutylaldehyde, 3,3-dimethylbutylaldehyde, caprylaldehyde, caprinealdehyde, and glutalaldehyde.

In addition, examples of the ketones having the ketone functional group may include acetone, butanone, pentanone, hexanone, cyclohexanone, and acetophenone.

Hereinafter, preferred examples are presented so as to help the understanding of the present invention. However, the following examples are for illustrative purposes only and the present invention is not limited by the following examples.

PREPARATION EXAMPLE

<Preparation Example> Nitric Acid Pre-Treatment of Carbon Carrier

Activated carbon and carbon black (carbon black B, carbon black A) were used as a support for a Ru—Sn catalyst. Each carbon carrier was pre-treated with a 5 wt % aqueous nitric acid solution at 95° C. for 3 hours before impregnating a Ru—Sn precursor.

Specifically, 30 g of each carbon carrier was stirred in 500 g of a 5 wt % aqueous nitric acid solution at 95° C. for 3 hours and then filtered. Washing was continuously performed with distilled water until pH of the filtered distilled water became 7. Each filtered carbon carrier was dried at 373K for 24 hours, and the physical properties of the carbon carrier pre-treated with nitric acid are shown in Table 1 below.

TABLE 1

| | Pore size (nm) | Micropore volume (cm$^3$/g) | Mesopore volume (cm$^3$/g) | BET specific surface are (m$^2$/g) |
|---|---|---|---|---|
| Activated Carbon | 7.5 | 0.22 | 0.44 | 770 |
| Carbon Black A | 13.6 | 0.06 | 0.98 | 307 |
| Carbon Black B | 4.92 | 0.04 | 0.35 | 229 |

EXAMPLES

<Example 1> High Concentration Nitric Acid Pre-Treatment of Carbon Black A Carrier In the case of carbon black A carrier, in addition to the pre-treatment using the 5 wt % aqueous nitric acid solution in the preparation example, pre-treatment was performed with 30 wt % and 50 wt % aqueous nitric acid solutions at 95° C. for 30 hours. Specifically, 30 g of carbon black A carrier was stirred in 500 g of a 30 wt % or 50 wt % aqueous nitric acid solution at 95° C. for 3 hours and then filtered. Washing was continuously performed with distilled water until pH of the filtered distilled water became 7. The filtered carbon black A carrier was dried at 373K for 24 hours. The results of nitrogen physical adsorption analysis of the carbon black A carrier pre-treated with nitric acid are shown in FIG. 1 and Table 2 below.

TABLE 2

| | Pore size (nm) | Micropore volume (cm$^3$/g) | Mesopore volume (cm$^3$/g) | BET specific surface area (m$^2$/g) |
|---|---|---|---|---|
| Carbon Black A - 5 wt % HNO$_3$ | 4.92 | 0.04 | 0.35 | 229 |
| Carbon Black A - 30 wt % HNO$_3$ | 4.75 | 0.05 | 0.38 | 213 |
| Carbon Black A - 50 wt % HNO$_3$ | 4.68 | 0.04 | 0.43 | 211 |

<Example 2> Production of Ru—Sn/Carbon Black A Catalyst Pre-Treated with 5 wt % Nitric Acid In the preparation example, Ru—Sn was supported on 10 g of carbon carrier of carbon black A, in which an aqueous solution in which 1.38 g of RuCl$_3$*3H$_2$O and 1.12 g of SnCl$_2$*2H$_2$O were dissolved in 7 g of H$_2$O was pre-treated with 5 wt % nitric acid, at room temperature by using incipient wetness impregnation. After drying at 373K for 12 hours, reduction was performed at 773K for 3 hours while flowing hydrogen (flow rate: 20 ml min$^{-1}$ g$^{-1}$), and it was cooled to room temperature while flowing hydrogen (flow rate: 20 ml min$^{-1}$ g$^{-1}$). After flowing helium (flow rate: 20 ml min$^{-1}$ g$^{-1}$) at room temperature for 30 minutes, the catalyst was immobilized while flowing 10% oxygen/nitrogen mixed gas (flow rate: 20 ml min$^{-1}$ g$^{-1}$) for 1 hour. The produced catalyst was denoted by "Ru—Sn/Carbon Black A".

<Example 3> Production of Ru—Sn/Carbon Black A Catalyst Pre-Treated with 30 wt % and 50 wt % Nitric Acids In the preparation example, Ru—Sn was supported on 10 g of carbon carrier of carbon black A, in which an aqueous solution in which 1.38 g of RuCl$_3$*3H$_2$O and 1.12 g of SnCl$_2$*2H$_2$O were dissolved in 7 g of H$_2$O was pre-treated with 30 wt % and 50 wt % nitric acids, at room temperature by using incipient wetness impregnation. After drying at 373K for 12 hours, reduction was performed at 773K for 3 hours while flowing hydrogen (flow rate: 20 ml min$^{-1}$ g$^{-1}$), and it was cooled to room temperature while flowing hydrogen (flow rate: 20 ml min$^{-1}$ g$^{-1}$). After flowing helium (flow rate: 20 ml min$^{-1}$ g$^{-1}$) at room temperature for 30 minutes, the catalyst was immobilized while flowing 10% oxygen/nitrogen mixed gas (flow rate: 20 ml min$^{-1}$ g$^{-1}$) for 1 hour.

The produced catalyst was denoted by "Ru—Sn/carbon black A (30 wt % $HNO_3$)" and "Ru—Sn/Carbon Black A (50 wt % $HNO_3$)".

<Example 4> Production of Ru—Sn/Carbon Black B Catalyst Pre-Treated with 5 wt % Nitric Acid In the preparation example, Ru—Sn was supported on 10 g of carbon carrier of carbon black B, in which an aqueous solution in which 1.38 g of $RuCl_3*3H_2O$ and 1.12 g of $SnCl_2*2H_2O$ were dissolved in 7 g of $H_2O$ was pre-treated with 5 wt % nitric acid, at room temperature by using incipient wetness impregnation. After drying at 373K for 12 hours, reduction was performed at 773K for 3 hours while flowing hydrogen (flow rate: 20 ml $min^{-1}$ $g^{-1}$), and it was cooled to room temperature while flowing hydrogen (flow rate: 20 ml $min^{-1}$ $g^{-1}$). After flowing helium (flow rate: 20 ml $min^{-1}$ $g^{-1}$) at room temperature for 30 minutes, the catalyst was immobilized while flowing 10% oxygen/nitrogen mixed gas (flow rate: 20 ml $min^{-1}$ $g^{-1}$) for 1 hour. The produced catalyst was denoted by "Ru—Sn/Carbon Black B".

COMPARATIVE EXAMPLE

<Comparative Example 1> Production of Ru—Sn/Activated Carbon Catalyst Pre-Treated with 5 wt % Nitric Acid In the preparation example, Ru—Sn was supported on 10 g of carbon carrier of activated carbon, in which an aqueous solution in which 1.38 g of $RuCl_3*3H_2O$ and 1.12 g of $SnCl_{2*2}H_2O$ were dissolved in 7 g of $H_2O$ was pre-treated with 5 wt % nitric acid, at room temperature by using incipient wetness impregnation. After drying at 373K for 12 hours, reduction was performed at 773K for 3 hours while flowing hydrogen (flow rate: 20 ml $min^{-1}$ $g^{-1}$), and it was cooled to room temperature while flowing hydrogen (flow rate: 20 ml $min^{-1}$ $g^{-1}$). After flowing helium (flow rate: 20 ml $min^{-1}$ $g^{-1}$) at room temperature for 30 minutes, the catalyst was immobilized while flowing 10% oxygen/nitrogen mixed gas (flow rate: 20 ml $min^{-1}$ $g^{-1}$) for 1 hour. The produced catalyst was denoted by "Ru—Sn/Activated Carbon".

[Experimental Example] Cyclohexanedicarboxylic Acid Conversion Experiment

A cyclohexanedicarboxylic acid conversion experiment was performed in a titania-lined stainless steel autoclave with a nominal volume of 250 ml and a maximum working pressure of 10.0 MPa. At this time, 3 g of a catalyst, 11.25 g of a reactant (cyclohexanedicarboxylic acid), and 150 g of a solvent ($H_2O$) were added, and the reaction was performed at 503K. Subsequently, the reactor was pressurized to a reaction pressure by using hydrogen, such that whether the reactor leaked was checked through a hydrogen detector. Oxygen inside the reactor was completely removed by depressurization and purging. Finally, the pressure inside the reactor was set to 10 bar, the reactor was heated to the reaction temperature, and the reactor was pressurized to the reaction pressure of the hydrogen atmosphere. Then, the reaction was performed for 6 hours. The reaction was performed at 90° C. and 90 bar for 6 hours, and the stirring was maintained at a speed of 1,000 rpm by using an overhead impeller. After the reaction, the reactor was cooled to room temperature and decompressed, such that the catalyst and the liquid product were separated by filtration and analyzed by gas chromatography with an HP-1 column.

Figure 2:
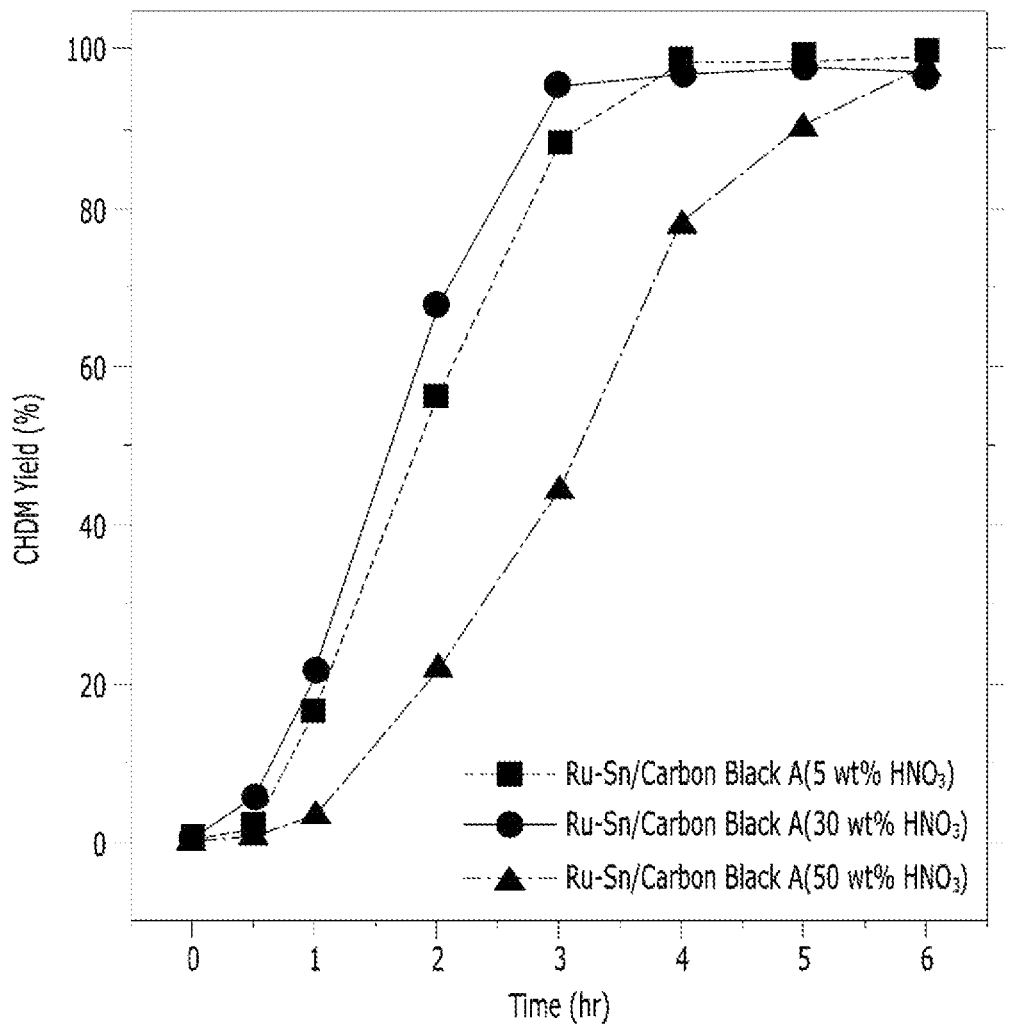
FIG. 2 is a graph showing catalytic activity for concentration of nitric acid pre-treatment of carbon black A carriers according to an embodiment of the present invention.

The results of the cyclohexanedicarboxylic acid conversion experiments using the catalysts produced according to Examples 2 to 4 and Comparative Example 1 are shown in FIG. 2 and Table 3.

TABLE 3

| Catalyst | CHDM yield (%) after 6-hour reaction |
|---|---|
| Ru—Sn/Carbon Black A | 99 |
| Ru—Sn/Carbon Black B | 84 |
| Ru—Sn/Activated Carbon | 10 |

As shown in FIG. 2 and Table 3, the activities of the Ru—Sn/carbon black A and Ru—Sn/carbon black B catalysts, which have a high ratio of mesopores among the total pores, are faster than the activity of the Ru—Sn/activated carbon catalyst, which has a low ratio of mesopores.

As shown in FIG. 2, the difference in the activity of the catalyst according to the nitric acid pre-treatment concentration of the carbon black A carrier can be confirmed. When the carbon black A carrier was pre-treated with the 30 wt % aqueous nitric acid solution according to Example 1, the catalyst activity is the fastest. The catalyst activity is higher in the order of the 5 wt % aqueous nitric acid solution and the 50 wt % aqueous nitric acid solution.

Although the present invention has been described with reference to the drawings according to embodiments of the present invention, it will be understood by those of ordinary skill in the art that various applications and modifications can be made thereto without departing from the scope of the present invention.

The invention claimed is:

1. A carbon-based catalyst enabling selective conversion, which is a hydrogenation catalyst comprising porous carbon as a carrier and an active metal supported on the carbon, wherein
   the carbon is 50% or more in a volume ratio of mesopores having a pore size of 2 nm to 50 nm among the total pores, and an amount of an active metal is in a range of 1 part by weight to 20 parts by weight based on 100 parts by weight of the carrier, and
   the carbon includes one or more selected from the group consisting of activated carbon, carbon black, graphite, graphene, ordered mesoporous carbon (OMC), and carbon nanotubes,
   wherein the active metal comprises:
   one or more noble metals selected from the group consisting of palladium (Pd), rhodium (Rh), ruthenium (Ru), and platinum (Pt); and
   one or more metals selected from the group consisting of tin (Sn), iron (Fe), rhenium (Re), and gallium (Ga).

2. The carbon-based catalyst of claim 1, wherein the noble metal is ruthenium, and the metal is tin.

3. The carbon-based catalyst of claim 1, wherein the carbon carrier is pre-treated with an aqueous nitric acid ($HNO_3$) solution.

4. The carbon-based catalyst of claim 3, wherein the aqueous nitric acid ($HNO_3$) solution includes 1 part by weight to 50 parts by weight of nitric acid based on 100 parts by weight of the solution.

5. The carbon-based catalyst of claim 1, wherein the carbon has a specific surface area of 100 $m^2$/g to 1,500 $m^2$/g and a pore volume of 0.1 ml/g to 1.5 ml/g.

6. The carbon-based catalyst of claim 1, wherein the carbon has a three-dimensional rod-shaped or three-dimensional tubular pore structure having ordered mesopores of 2 nm to 25 nm.

7. A hydrogenation method comprising hydrogenating a carboxylic acid group to an alcohol group in the presence of the catalyst according to claim 1.

8. A method for producing the carbon-based catalyst enabling high selective conversion according to claim 1, wherein the carbon carrier is pre-treated with an aqueous nitric acid ($HNO_3$) solution including 1 part by weight to 50 parts by weight of nitric acid one or more times.

9. The method of claim 8, wherein the pre-treatment process is performed in a temperature range of 50° C. to 150° C.

10. The method of claim 8, wherein the pre-treatment process is performed for 1 hour to 10 hours.

11. The method of claim 8, wherein the pre-treatment process is performed before the active metal is supported.

12. A hydrogenation method comprising hydrogenating a carboxylic acid functional group, an aldehyde functional group, or a ketone functional group to an alcohol functional group in the presence of the catalyst according to claim 1.

13. The hydrogenation method of claim 12, wherein the carboxylic acid includes oxalic acid, malonic acid, succinic acid, glutaric acid, adipic acid, pimelic acid, suberic acid, azelaic acid, sebacic acid, phthalic acid, isopthalic acid, terephthalic acid, formic acid, acetic acid, caproic acid, caprylic acid, lauric acid, myristic acid, palmitic acid, stearic acid, isostearylic acid, oleic acid, maleic acid, cyclohexane carboxylic acid, and benzoic acid.

14. The hydrogenation method of claim 12, wherein aldehydes having the aldehyde functional group include formaldehyde, propionaldehyde, n-butylaldehyde, isobutylaldehyde, valeraldehyde, 2-methylbutylaldehyde, 3-methylbutylaldehyde, 2,2-dimethylpropionaldehyde, caproaldehyde, 2-methylvaleraldehyde, 3-methylvaleraldehyde, 4-methylvaleraldehyde, 2-ethylbutylaldehyde, 2,2-dimethylbutylaldehyde, 3,3-dimethylbutylaldehyde, caprylaldehyde, caprinealdehyde, and glutalaldehyde.

15. The hydrogenation method of claim 12, wherein ketones having the ketone functional group include acetone, butanone, pentanone, hexanone, cyclohexanone, and acetophenone.

16. A hydrogenation method comprising hydrogenating a carboxylic acid functional group, an aldehyde functional group, or a ketone functional group to an alcohol functional group in the presence of a hydrogenation catalyst comprising porous carbon as a carrier and an active metal supported on the carbon,
  wherein a hydrogenation reaction pressure is 2 MPa to 15 MPa, a reaction temperature is 140° C. to 280° C., and a reaction time is 0.5 hours to 10 hours, and
  the carbon is 50% or more in a volume ratio of mesopores having a pore size of 2 nm to 50 nm among the total pores, and an amount of an active metal is in a range of 1 part by weight to 20 parts by weight based on 100 parts by weight of the carrier.

\* \* \* \* \*